United States Patent
Kerfoot, Jr.

[11] 3,976,077
[45] Aug. 24, 1976

[54] EYE SURGERY DEVICE

[76] Inventor: Franklin W. Kerfoot, Jr., 678 Andover Road, Newtown Square, Pa. 19073

[22] Filed: Feb. 3, 1975

[21] Appl. No.: 546,591

[52] U.S. Cl. .............................. 128/305; 308/121
[51] Int. Cl.² ...................... A61B 17/32; A61F 9/00
[58] Field of Search ............. 128/305; 308/9, 121, 308/122, 140, 141, 149, 168, 170, 187, 246, DIG. 1

[56] References Cited
UNITED STATES PATENTS

| | | | |
|---|---|---|---|
| 908,539 | 1/1909 | Beutler | 308/141 X |
| 2,584,770 | 2/1952 | Wilcock | 308/9 |
| 3,639,074 | 2/1972 | Killick | 308/DIG. 1 |
| 3,736,938 | 6/1973 | Evvard et al. | 128/305 |
| 3,835,858 | 9/1974 | Hagen | 128/305 |

*Primary Examiner*—Channing L. Pace
*Attorney, Agent, or Firm*—Caesar, Rivise, Bernstein & Cohen, Ltd.

[57] ABSTRACT

An ophthalmic surgical device including a housing having an extension sleeve projecting from one end thereof. A rotary shaft, having helical threads at one end thereof, which threads terminate in a cutting tip, is disposed within the extension sleeve with the tip being exposed at the free end of the sleeve. The shaft is mounted within three fluid-lubricated sleeve bearings. One of the bearings is mounted within the sleeve adjacent to the tip thereof with its central axis offset and slightly angled with respect to the axes of the other bearings to effect the bending and slight loading of the shaft. The bearings are lubricated by water provided under pressure thereto and serve to enable the shaft to rotate at a high rate of speed under the force provided by an air turbine. Means are provided for supplying a working fluid to the cutting tip of the device to aid in the maceration of the material to be removed by the tool. The macerated material and the working fluid are withdrawn from the operative site by the pumping action of the rotating helical threads of the shaft. The water pressure on the bearings not only lubricates the bearings but also precludes the macerated material and working fluid from being pumped into the interior of the housing.

25 Claims, 7 Drawing Figures

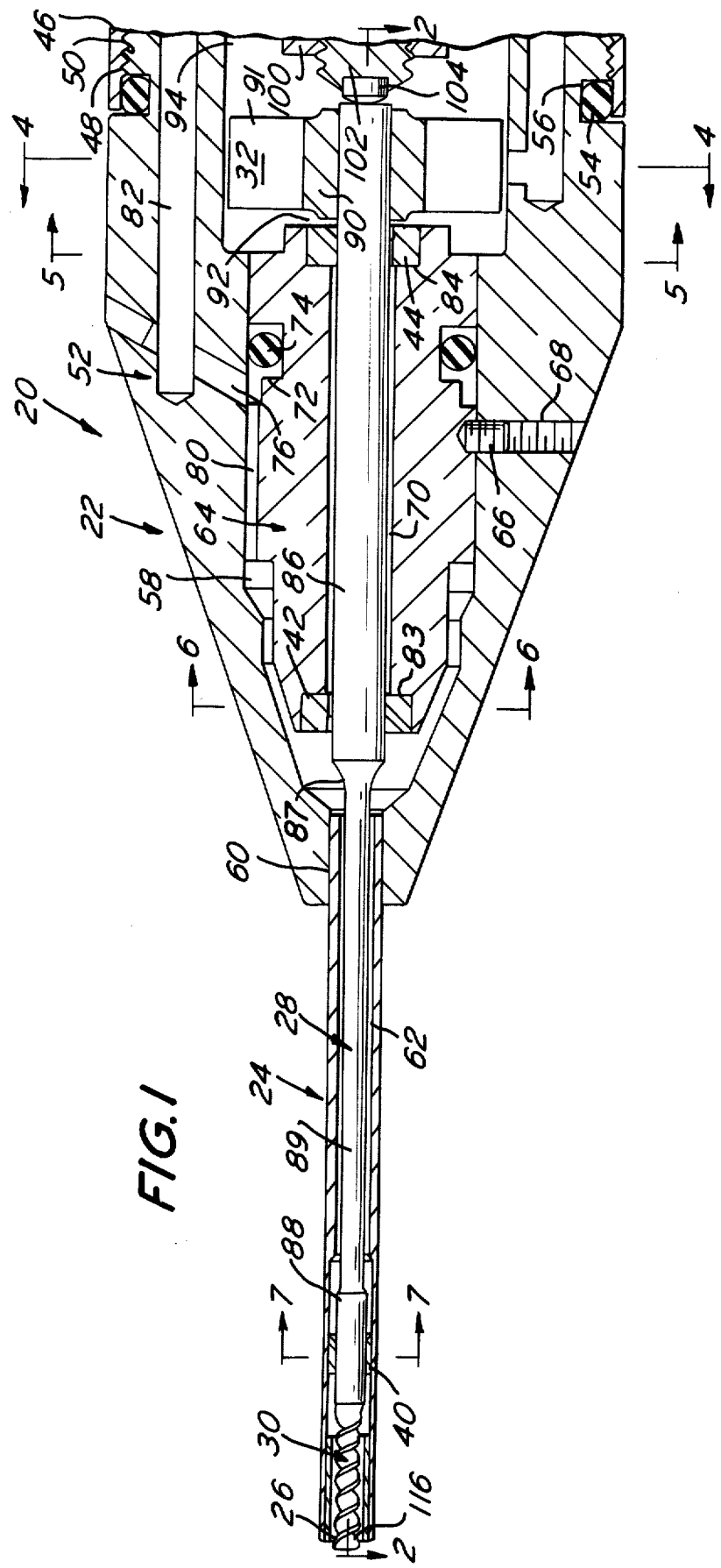

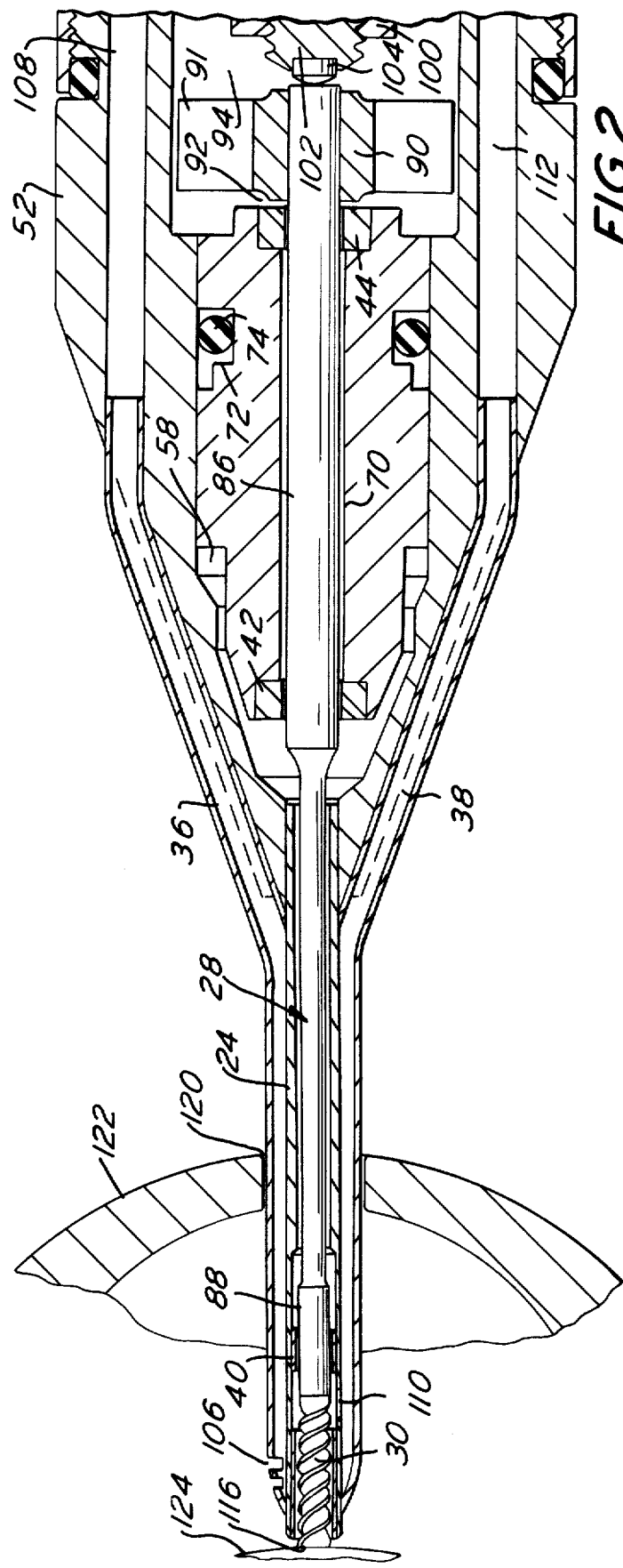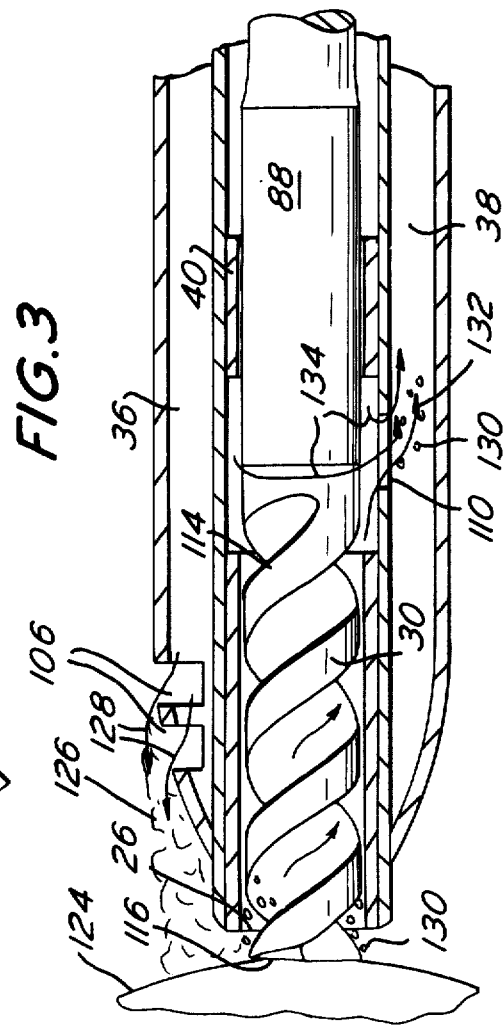

EYE SURGERY DEVICE

This invention relates generally to surgical devices and more particularly to ophthalmic surgery devices.

A recent development in ophthalmic surgery has obviated the use of conventional cutting instruments, e.g., scalpels, for effecting the removal of unwanted tissue, such as lens opacities. To that end, macerating type surgical devices are now used in cataract surgery to effect the removal of lens opacities by the use of a rotary bur which grinds away the opacities. Such devices also serve to withdraw the ground or macerated material from the operating site via suction means. For example, in U.S. Pat. No. 3,736,938 (Evvard et al) a surgical device is disclosed which supplies a working liquid to the cutting site while a high speed rotary cutter effects the maceration of the material thereat. At the same time a tube disposed about the cutter vibrates ultrasonically to coact with the cutter in macerating the lens. The cutter includes spiral grooves which effect the evacuation of the liquid and the macerated lens material.

In U.S. patent application Ser. No. 397,478, filed on Sept. 14, 1973 and assigned to National Aeronautics and Space Administration, there is disclosed a macerating surgical device which overcomes various disadvantages of the prior art in effecting the removal of the macerated lens material and yet does not utilize ultrasonic energy (whose effects on the eye are not fully known).

To that end, that device comprises a housing having an extension including a sleeve through which the free end of a rotary shaft extends. The free end includes helical threads terminating in a cutting tip. The shaft is connected to an air turbine motor to effect its rotation within the extension at an extremely high speed. Plural conduits are provided to carry treatment fluid. e.g., saline solution, to the operative site. The rotation of the cutting tip serves to grind up the eye tissue to be removed with the helical threads on the shaft act as a pump to pump the macerated tissue and treatment fluid away from the operative site through communicating passageways in the extension and into a collector.

As a result of the high speed rotation of the shaft and the close tolerance between the shaft and the sleeve in the extension, macerated material and liquid is pumped up into the space therebetween. In order to preclude the ingress of such material between the shaft and sleeve extension, a counter flow pump is provided. The pump is formed by a second screw thread on the shaft. The second threaded portion also has spiral grooves but their pitch is opposite to the pitch of the screw portion at the tip of the shaft. Accordingly, the rotation of the shaft and the concomitant rotation of the second threaded portion effects a reverse pumping action to cause the treatment fluid and macerated material to flow between the shaft and the extension and back toward the screw portion at the tip thereof. This action flushes any macerated material from the space between the shaft and the extension.

While the counter action pump technique used in the aforenoted patent application is generally effective to preclude the ingress of the macerated material and treatment fluid into the space between the rotating shaft and the sleeve in which it rotates, some material may nevertheless gain access to such space, with the deleterious effect of hardening therein to cause the shaft to bind. In addition, the use of a counter action pump results in a rather complex and hence expensive surgical device.

Accordingly, it is a general object of this invention to provide a device which overcomes the disadvantages of the prior art.

It is a further object of this invention to provide a surgical cutting device suitable for high speed cutting in very small openings in the body.

It is still a further object of this invention to provide a surgical device for removing cut or macerated material by a pumping action, while precluding the ingress of such material into the interior of the device in a simple and expeditious manner.

It is still a further object of this invention to provide a surgical device utilizing a rotary tool mounted in fluid-lubricated bearings.

It is yet a further object of this invention to provide a stable bearing and shaft system for high speed rotary cutting or pumping devices utilizing fluid-lubricated sleeve bearings.

These and other objects of the invention are achieved by providing a surgical device comprising a housing and a sleeve having an open free end and connected to the housing. A shaft is positioned within the housing and the sleeve, with the shaft having a free end disposed adjacent the free end of the sleeve. The free end of the shaft is in the form of a tool adapted to operate in conjunction with a working fluid at the free end of the sleeve. The shaft is rotatably mounted within a first fluid-lubricated sleeve bearing and second fluid-lubricated bearings means. The first bearing is positioned within the elongated sleeve. Means are provided for supplying a liquid under pressure to the first bearing and the second means, with the liquid under pressure in the elongated sleeve lubricating the first bearing within the sleeve and precluding the ingress of the working fluid through the elongated sleeve and into the housing.

Other objects and many of the attendant advantages of this invention will be readily appreciated as the same becomes better understood by reference to the following detailed description when considered in connection with the accompanying drawings wherein:

FIG. 1 is a side elevational view, partially in section, of a portion of the surgical device in accordance with this invention;

FIG. 2 is a top elevational view, partially in section, of a portion of the device shown in FIG. 1 when operating on an eye;

FIG. 3 is an enlarged sectional view of a portion of the working tip of the device shown in FIGS. 1 and 2;

Figure 4:
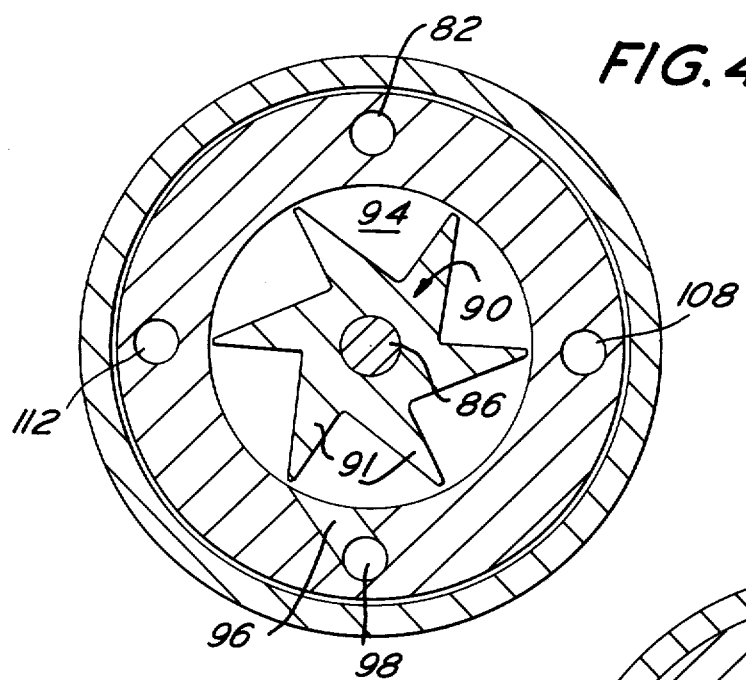
FIG. 4 is a sectional view taken along line 4—4 of FIG. 1.

Referring now to the various figures of the drawing wherein like reference characters refer to like parts, there is in FIG. 1 as improved surgical device 20. The device 20 is arranged for cutting away bodily material through very small openings in the body and has particular utility in opthamalic surgery applications, such as cataract removal.

As can be seen in FIG. 1 the device 20 basically comprises a housing 22 terminating in an extending sleeve 24 having an open free end 26. A shaft or rotor 28 is disposed within the housing 22 and the sleeve 24 and includes a tool 30 at its free end disposed adjacent opening 26. The tool 30 is adapted to be rotated at a high speed, e.g. 300,000 rpm, to grind or otherwise macerate bodily material (tissue or bone) upon contact therewith. The tool is rotated at the high speed by motor means 32 disposed within the housing and connected to one end of the shaft 28.

In order to aid in the maceration of the bodily material a working fluid 126 (FIG. 3), such as a sterile saline solution is supplied to the cutting site via passageways 36 attached to sleeve 24. The fluid 126 also serves as the vehicle for carrying away the ground or macerated material from the cutting site.

The shaft 28 is mounted for high speed rotation within a fluid-lubricated bearing system including three spaced sleeve bearings 40, 42 and 44. As is known fluid-lubricated sleeve bearings serve to support rotary shafts therein on a film of lubricated fluid interposed between the sleeve and the shaft to enable the shaft to rotate with very little friction.

In accordance with the preferred embodiment of this invention, the bearings 40, 42 and 44 are lubricated by sterile water provided thereto under high pressure, e.g., 30 psi, from means (not shown). This construction eliminates the need for oil or grease lubrication to provide a readily sterilizable and hygienic surgical device. In addition, the water lubricated bearings run quieter than ball bearings.

The sterile water provided to the bearing system for lubrication, by virtue of the high pressure on the water, also serves to preclude the ingress of foreign material, e.g., macerated tissue, dust, etc., into the interior of the housing through the space between the sleeve and the shaft. Accordingly, the device of this invention eliminates the need for complex sealing techniques, such as the counter flow pump technique disclosed in the aforenoted patent application.

As is known, lightly loaded bearings or bearings lubricated with a low viscosity fluid and operated at high speeds are particularly susceptible to entering the unstable rotary condition, commonly known as half frequency whirl or spin. In such a condition, the central axis of the shaft orbits around the central axis of the bearings as the shaft rotates and the minimum thickness of the lubricating film falls to zero, whereupon the load carrying capacity of the bearing vanishes and the shaft binds.

Since the surgical device 20 of this invention utilizes a high speed shaft mounted in water (a low viscosity fluid) lubricated bearings and since, as will be described in detail later, the shaft is of very small diameter and lightly loaded during the delicate surgical operation, the prevention of half frequency whirl is of utmost importance.

Heretofore, half frequency whirl has been prevented through the use of various complex techniques, such as the use of the elliptical sleeve bearings, rotatable pressure pads, etc. In the instant invention such complex techniques are obviated by the inventive expedient of misaligning the bearings. To that end, as will be described in considerable detail later, the bearings 40, 42 and 44 of the bearing system are misaligned to produce a calculated load therein and a concomitant stress in the shaft. It has been found that such action effectively precludes the lightly loaded, high speed, water lubricated shaft from commencing half speed whirl.

A more detailed description of the device 20 follows. As can be seen in FIG. 1 the housing 22 is formed of a cylindrical member 46 (only a portion of which is shown), which serves as the portion to be gripped by the operator and in this regard is referred to as the handpiece of the device. The handpiece 46 terminates in a threaded portion 48 for mating engagement with a threaded portion 50 of a housing tube assembly 52. An O-ring 54 is disposed within a recess 56 cut in the periphery of portion 50 and is interposed between portions 48 and 50 to prevent the egress of liquid through the interface.

The housing tube assembly 52 is a conically shaped member defining a hollow spaced interior 58 therein and terminates at its pointed end in an opening 60. One end of the elongated sleeve 24 is mounted within the opening 60 and is secured in place as by soldering.

As can be seen in FIGS. 1 and 2 the sleeve 24 is an elongated tubular member having a central passageway 62 extending through its entire length and communicating with the interior 58 in the assembly 52.

A sleeve and bearing assembly 64 is mounted within the hollow interior 58 of the assembly 52 and is secured in place therein via a set screw 66 extending through a threaded opening 68 in the assembly 52. The assembly 64 is of generally cylindrical shape and substantially conforms to the shape of the interior 58 of the assembly 52. The assembly 64 includes a central passageway 70 extending through its entire length and coaxial with the passageway 62 in the sleeve 24 to enable the rotary shaft 28 to extend therethrough.

A stepped annular recess 72 is provided about the exterior of assembly 64 and O-ring 74 is disposed therein and interposed between the recess and the wall of the interior of assembly 52. The O-ring 74 serves as a liquid seal to preclude the high pressure water from gaining access to the interior of the housing past the seal.

As can be seen in FIG. 1, the housing tube assembly 52 includes a passageway 76 therein for carrying high pressure water. As noted heretofore, such water serves as the lubrication for the bearings and acts as a seal to prevent the ingress of foreign matter into the interior of the housing. The passageway 76 communicates with the portion of the stepped annular recess 72 forward of the O-ring seal 74. A recess 80 is cut longitudinally along the surface of the assembly 64 to provide a passageway communicating with passageway 76 to carry the water therefrom and into the interior space 58 within assembly 52. Another passageway 82 is provided within the housing tube assembly 52 and extends longitudinally therethrough and into communication with a tube (not shown) for carrying the high pressure water from a source (not shown) to the passageway 76.

The sleeve and bearing assembly 64 serve to mount two of the three bearings of the system therein, those being bearings 42 and 44. To that end, assembly 64 includes a pair of recesses 83 and 84 cut into the central passageway 70 contiguous with the ends of the assembly. The recess 83, see FIG. 1, serves to hold sleeve bearing 42 while the recess 84 holds sleeve bearing 44.

The bearings are formed of tungsten carbide, with the area of bearing 42 being larger than the area of bearing 44 but with the inside diameter of the bearings being the same. The recesses 82 and 84 are disposed in such a manner that the central axes of the respective bearings 42 and 44 mounted therein are coaxial.

The sleeve bearing 40 is also formed of tungsten carbide and is mounted within the central passageway 62 of the sleeve 24 adjacent the open free end 26 thereof.

As will be described in detail later, sleeve 24 is bent along its central axia so that the axis of sleeve bearing 40 mounted therein is slightly offset and angled from the coaxial central axes of the bearings 42 and 44 in the housing 22.

The shaft 28 is an elongated rod-like member formed of tungsten carbide and includes two different diameter portions, a larger or major diameter portion 86 and a smaller or minor diameter portion 88. The interface of the major and minor diameter portions is defined by a curved surface 87. The minor diameter portion includes a portion 89 which is undercut to enhance flexibility. The shaft is mounted within the bearings with the major diameter portion 86 extending through the coaxial bearings 42 and 44, hereinafter referred to as the middle and rear bearings, respectively, and with the minor diameter portion 88 extending through bearing 40, hereinafter referred to as the front bearing.

Figure 5:
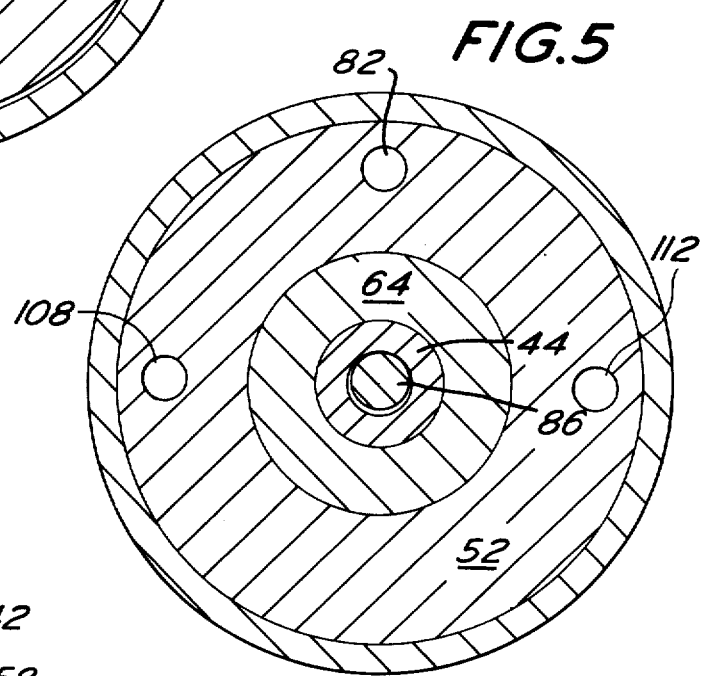
FIG. 5 is a sectional view taken along line 5—5 of FIG. 1.
Figure 6:
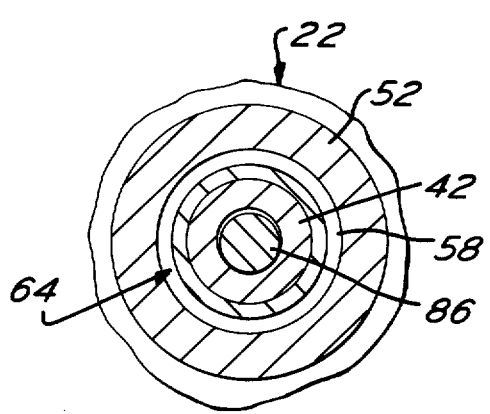
FIG. 6 is a sectional view taken along line 6—6 of FIG. 1.
Figure 7:
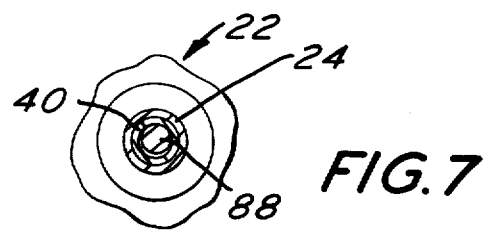
FIG. 7 is a sectional view taken along line 7—7 of FIG. 1.

The offsetting of the front bearing with respect to the middle and rear bearings have the effect of bending the shaft slightly such that respective portions of the shaft make contact with respective interior peripheral portions of the bearings through which the shaft passes when the shaft is stationary. This characteristic can be seen clearly in the cross-sectional views of FIGS. 5, 6 and 7. For example, as can be seen in the cross-sectional view of FIG. 5, the shaft 28 is bent such that the top peripheral surface of the major diameter portion 86 of the shaft passing therethrough (i.e., the journal), contacts the upper peripheral edge of the interior of the rear bearing 44 while the clearance between the bottom periphery of the journal and the bottom periphery of the bearing is increased. In a similar manner, as can be seen in the sectional view of FIG. 7, the upper periphery of the minor diameter portion 88 of the shaft passing through the front bearing 40 abuts the upper periphery of said bearing while the clearance between the lower periphery of the shaft and the corresponding portion of the bearing is increased. The upward displacement of the shaft with respect to the central axis of the front and rear bearings as described with respect to FIGS. 5 and 7 is accompanied by the downward displacement of the major diameter portion 86 of the shaft with respect to the middle bearing 42. For example, as can be seen in FIG. 6, the bottom periphery of the major diameter portion of the shaft 86 extending through middle bearing 42 contacts the corresponding interior periphery of said bearing while the clearance between the upper portion of the periphery of the shaft and the corresponding interior periphery of the bearing is increased.

The bending of the shaft has the effect of loading the bearing sufficiently to preclude the production of half speed whirl as the shaft is rotated within the bearing.

As the shaft begins rotating the journal portion of the shaft move out of contact with the associated peripheral portions of the bearings and a thin film of lubricating fluid, i.e., water, is formed between the closely adjacent portions, whereupon the shaft is able to rotate freely and stably.

The bending of the shaft to misalign the bearings is accomplished as follows for a device whose nominal major shaft diameter is 0.062 inch (1.58 mm), whose nominal minor shaft diameter is 0.040 inch (1.02 mm), whose front bearing is spaced from the middle bearing by 0.813 inch (20.7 mm), whose middle bearing is spaced from the rear bearing by 0.577 inch (14.6 mm), whose nominal front, rear and middle bearing lengths are 0.04 inch (1.02 mm), 0.044 inch (1.12 mm) and 0.025 inch (0.635 mm), respectively, and whose nominal front, middle and rear bearing diameters are 0.04 inch (1.02 mm), 0.062 inch (1.58 mm) and 0.062 inch (1.58 mm), respectively. The first step in the bending operation occurs with the shaft removed wherein the front bearing is bent downward to offset its center by 0.00085 inch (0.022 mm) nominally from the center line of the middle and rear bearings. The front bearing is then lapped to size in line with a point approximately at the mid point between the middle and rear bearings. The shaft is then bent downward again until the total eccentricity, that is the eccentricity between the center point on the central axis of the front bearing 40 and the coaxial central axis of the middle and rear bearings 42 and 44, is approximately 0.0026 inch to 0.0029 inch (0.066 mm to 0.074 mm) with the bending being accomplished at an area approximately 0.5 inch (12.7 mm) nominally from the center point of the front bearing 40. The shaft is then inserted in the bearing system.

Assuming that the shaft is rotated at about 300,000 rpm on a film of water in the bearings the following is noted, the combined action of the dynamic effects of the rotating shaft coupled with the resiliency of the shaft against the force created by the misaligned bearings, has the effect of bending the front end of the shaft downward to be eccentric with the rear of the shaft by approximately 0.0012 to 0.0018 inch (0.031 to 0.046) mm) nominally. This eccentricity produces a bearing load in the front bearing equivalent to approximately 40 to 60 psi (2.81 to 4.22 kg/cm$^2$) and somewhat higher load in pressure on the rear bearings, with an average water film thickness of 0.00025 inch (0.0064 mm) and a minimum film thickness of approximately 0.00005 inch (0.0013 mm) in each bearing when running at 300,000 rpm. In addition, the shaft is bent such that the journal thereof in the front bearing remains essentially parallel to the front bearing.

The rotation of the shaft at the high speed is effected via motor means 32. In accordance with the preferred embodiment of this invention the motor comprises an air turbine rotor 90 having six fins or vanes 91 projecting therefrom (see FIG. 4). The rotor is connected to the rear end of the shaft 28 in a manner so as to provide a small clearance 92 between it and the end face of bearing 44. The clearance enables the longitudinal positioning of the shaft to be manually adjusted by means, to be described later, yet is sufficiently small to prevent excessive forward travel. The rotor 90 is disposed within a circular cavity 94 within assembly 52. High pressure air is provided to the interior of the cavity for effecting the rotation of the rotor 90 therein. To that end, as can be seen in FIG. 4, a passageway 96 is provided in assembly 52 and extends at an anle to the shaft. High pressure air is provided through the passageway to impact the vanes of the rotor at an angle having a component tangential to the axis of rotation of the rotor to cause the rotation thereof. A longitudinally extending passageway 98 is provided within assembly 52 and communicates with passageway 96. The passageway 98 is coupled to a high pressure air line (not shown) and serves to carry high pressure air provided therethrough from a source (not shown).

The longitudinal positioning of the shaft 28 and hence the cutter 30 is effected by a finger control (not shown) and associated components, only a portion of which are shown. Such components include a sliding member 100 adapted to be moved, under the control of a finger switch, lonitudinally within the housing 22. A threaded insert 102 is mounted within the member 100. A jeweled thrust bearing 104, such as a ruby bearing, is mounted within insert 102 and coaxial with the axis of the shaft 28. The bearing is arranged to abut the flat rear end 106 of the shaft to apply pressure thereto and effect the movement thereof through the distance established by the clearance 92.

As will be appreciated by those skilled in the art, the high pressure water in interior 58 operates against the major diameter portion and minor diameter portion therein to produce a net longitudinal thrust force in the rearward direction and thereby precludes the accidental extension of the tip 30 out of the open end 26 of the sleeve 24. The thrust bearing 104 serves to take up the rearward thrust produced on the shaft.

As noted heretofore, passage means 36 are provided to carry a working liquid, such as a saline solution, to the operating site, which liquid serves as the vehicle for carrying the macerated material away from the site. To that end, the device includes outlet passage means 38 which serve to carry the macerated material and the liquid vehicle from the operating site to collections means. As can be seen in FIG. 3, the passageway 36 comprises a tubular line lying along one side of the sleeve 24. The line terminates immediately adjacent the open end of the sleeve and includes a pair of outlet ports 106 therein. The line also extends along the conical housing tube assembly 52 and terminates at its other end in a longitudinally extending communicating passageway 108 within assembly 52. A line (not shown) is provided connected to passageway 108 for providing a saline solution from the means (not shown) to line 108 and from there through passageway 36, and outlet ports 106 to the operating site. The return passage 38 is constructed in a similar manner to passage 36 and lies on the opposite side of the sleeve and the conical portion of the housing tube assembly 52. An opening 110, hereinafter referred to as a return port, is provided in the wall of sleeve 24 immediately in front of bearing 40. The return port 110 serves to carry macerated material and its carrier liquid from the operating site under the pumping force produced by the rotating tool 30 and into the passageway 38. The passageway 38 is connected to a longitudinally extending passage 112 provided within housing tube assembly 52 and in communication therewith for providing the macerated material and liquid carrier into passageway 112. A return line (not shown) is provided coupled to line 112 to carry the macerated material and liquid carrier to collection means (not shown).

In accordance with the preferred embodiment of this invention, the tool 30 serves as both a cutting implement for effecting the grinding or maceration of bodily material as well as a pump for carrying such material away from the operating site. To that end, as can be seen in FIG. 3, the tool 30 is in the form of a helical screw having helical threads 114 extending thereabout. The free end of the tool terminates in a cutting tip 116. As will be appreciated, the rotation of the shaft and the concommitant rotation of the screw threads 114 results in the creation of a pumping action by the tool, whereupon particulate material at the operating site is carried by the rotating threads through the opening 26 in the tip of the sleeve and downward through the sleeve to communicating return port 110 to enable the material to pass therethrough and into passageway 38. The pressure produced by such pumping action is of the order of 5 psi (0.33 kg/cm$^2$) and considerably less than the fluid bearing pressure. Since the bearing water pressure is substantially higher than the pressure produced by the pumping action of the rotating tool, a positive flow of water occurs from the interior 58 of the housing tube assembly 52, downward through the space between the shaft 28 and the sleeve 24 and through front bearing 40 to the front end of the sleeve from whence it enters return port 110. Accordingly, foreign matter is prevented from gaining access to the interior of the device by the utilization of the high pressure water which serves as the lubricating and cooling means for the bearing system. Such an arrangement obviates the need of complex sealing systems which have characterized prior art devices.

Water leaking rearwardly through the rear bearing 44 and into cavity 94 is atomized by the high speed rotation of the rotor 90 therein. The spent air and atomized water within the cavity escapes through passage means (not shown) for release to the atmosphere.

In FIGS. 2 and 3 there is shown the use of the device in operation during the removal of opacities in the crystalline lens in an eye. To that end, the sleeve of the device is inserted within a small opening 120 in the limbus cornea of the eye and is extended therethrough until the free end of the sleeve contacts the opacity to be removed from lens 124. The finger control is then moved to cause the thrust bearing 104 to apply an axial force in the forward direction to the shaft to effect the extension of the cutting tip 116 slightly out of the open end 26 of the sleeve. In accordance with the preferred embodiment of this invention, the primary functions in cataract surgery of grinding and pumping the lens out can be accomplished with the shaft 116 protruding slightly, e.g. 0.01 inch (0.25 mm), as shown in FIG. 3. Since the crystalline lens of the eye is convex, the tip 116 of the tool 30 can even be slightly retracted within the open end of the sleeve and still effect the grinding or maceration of the lens portion 124.

The turbine is turned on to effect the rotation of the shaft while the saline solution, denoted by the reference numeral 126, is forced outward through passageway 36 and ports 116 in the direction of arrows 128. The macerated lens material produced at the operating site is denoted by the reference numeral 130 and is carried by the saline solution under the influence of the pumping action of the rotating tool 30 into the sleeve and from there through port 110 in the direction of arrow 132 into return line 38. Lubricating water at a higher pressure passes through bearing 40 in the direction of arrows 134 and into port 110 for removal along with the saline solution and the macerated lens material. Accordingly, all liquids and solid material are drawn away from the operating site during the operation of device 20.

It should be pointed out at this juncture that while the device as described heretofore is particularly suitable for ophthalmic surgical applications, it is to be understood that the device can be dimensioned and configured in various other ways for use in other surgical applications as either a cutting and grinding device, a pumping device or a combined grinding and pumping device.

As should be appreciated from the foregoing, the instant invention provides a surgical device enabling the quick, safe and efficient removal of bodily material via the use of a high speed rotary tool mounted within a fluid-lubricated stable and unsealed bearing system.

Without further elaboration, the foregoing will so fully illustrate my invention that others may, by applying current or future knowledge, readily adapt the same for use under various conditions of service.

What is claimed as the invention is:

1. Eye surgery apparatus comprising a shaft having a free end in the form of a tool, means for rotating said shaft at a high rate of speed at which half frequency whirl could occur and a bearing system including a first fluid-lubricated sleeve bearing and second fluid-lubricated sleeve bearing means, said first bearing being mounted with its central axis offset and slightly angled with respect to the central axis of said second bearing means, said shaft extending through said first bearing and said second bearing means, said shaft being bent slightly and loaded by said offset first bearing, whereby respective portions of said shaft make contact with respective portions of the interior periphery of said first bearing and second bearing means when said shaft is stationary and move out of contact therewith to ride with very little friction on a layer of lubricating fluid interposed between the shaft and the interior periphery of the first bearing and second bearing means when the shaft is rotating at a high speed, to preclude the shaft from entering the unstable condition wherein its central axis orbits around the central axis of said first bearing or said second bearing means as the shaft rotates.

2. The apparatus of claim 1 wherein said second bearing means comprise second and third fluid-lubricated sleeve bearings.

3. The apparatus of claim 2 wherein said second and third bearings are spaced from each other with their central axes being coaxial.

4. The apparatus of claim 3 wherein said lubricating fluid is water.

5. The apparatus of claim 4 wherein said apparatus also includes a housing and a sleeve extending therefrom and including an open free end, and said shaft and bearing system being mounted within said housing and said sleeve, with said shaft passing through said sleeve such that the free end of the shaft is disposed adjacent the free end of the sleeve, and at least one of said bearings being mounted within said sleeve.

6. The apparatus of claim 5 wherein said sleeve is bent slightly to therby offset the bearing mounted therein from the remaining bearings of the apparatus.

7. The apparatus of claim 6 wherein the water is provided in the housing under pressure to lubricate the bearings and to prevent the ingress of foreign matter through the sleeve and bearing mounted therein into the interior of the housing.

8. The apparatus of claim 6 wherein the tool includes helical threads.

9. The apparatus of claim 8 wherein said tool is a cutting bit.

10. The apparatus of claim 6 wherein said second and third bearings are mounted within said housing and wherein said first bearing is mounted within said bent sleeve adjacent the free end thereof.

11. The apparatus of claim 6 wherein the means for rotating said shaft comprises a turbine, said turine being connected to said shaft and being air driven.

12. The apparatus of claim 11 wherein the shaft is longitudinally slidable within said sleeve to expose the tool at the free end thereof.

13. The apparatus of claim 12 wherein the tool includes helical threads.

14. The apparatus of claim 13 wherein said tool is a cutting bit.

15. The apparatus of claim 14 wherein said shaft includes an increased diameter portion within said housing and against which said water pressure operates to produce a longitudinal force on said shaft in the direction of said housing.

16. The apparatus of claim 15 wherein said housing includes a thrust bearing in contact with said shaft.

17. The appapratus of claim 7 additionally comprising first means carrying a working liquid to the free turbine of the sleeve and second means carrying said liquid, any foreign matter picked up thereby and lubricating fluid away from said free end.

18. The apparatus of claim 17 wherein the means for rotating said shaft comprise a turbine, said turgine being connected to said shaft and being air driven.

19. The apparatus of claim 18 wherein said shaft is longitudinally slidable within said sleeve to expose said tool at the free end thereof.

20. The apparatus of claim 17 wherein said tool includes helical threads which act as a pump when said shaft is rotating.

21. The apparatus of claim 20 wherein an opening is provided in said sleeve adjacent said helical thread and communicating with said second passageway, whereupon the working liquid, foreign matter and lubricating fluid at the free end of the sleeve are pumped by the rotation of the shaft into the sleeve, through the opening therein and into said second passageway.

22. The apparatus of claim 20 wherein said tool is a cutting bit.

23. The apparatus of claim 21 wherein said bearing system includes three sleeve bearings, with two of said bearings being mounted within said housing and with the remaining bearing being mounted within said sleeve adjacent the free end thereof.

24. A surgical device comprising a housing, a sleeve connected to said housing, said sleeve having an open free end, a shaft positioned within said housing in said sleeve, said shaft having a free end disposed adjacent the free end of the elongated sleeve, the free end of the shaft being in the form of a helical thread cutting bit operating in conjunction with a working liquid at the free end of the elongated sleeve, said shaft being rotatably mounted within a first fluid-lubricated sleeve bearing and second fluid-lubricated sleeve bearing means, with said first bearing being positioned within said elongated sleeve, means for supplying the liquid under pressure to said first bearing and said second bearing means, with said liquid under pressure in said elongated sleeve lubricating said first bearing within said elongated sleeve and precluding the ingress of said working fluid through said elongated sleeve and into said housing, first passage means carrying said working liquid to the free end of the elongated sleeve and seconnd means carrying said liquid, any foreign matter picked up thereby and lubricating fluid away from said free end, said shaft being rotated by an air driven turbine connected thereto.

25. The device of claim 24 wherein said shaft is longitudinally slidable within said sleeve to expose said tool at the free end thereof.

* * * * *